United States Patent
Hoss et al.

(10) Patent No.: US 10,905,364 B2
(45) Date of Patent: Feb. 2, 2021

(54) ANALYTE LEVEL CALIBRATION USING BASELINE ANALYTE LEVEL

(71) Applicant: Abbott Diabetes Care Inc., Alameda, CA (US)

(72) Inventors: Udo Hoss, Castro Valley, CA (US); Erwin S. Budiman, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 628 days.

(21) Appl. No.: 15/310,691

(22) PCT Filed: May 14, 2015

(86) PCT No.: PCT/US2015/030880
§ 371 (c)(1),
(2) Date: Nov. 11, 2016

(87) PCT Pub. No.: WO2015/175828
PCT Pub. Date: Nov. 19, 2015

(65) Prior Publication Data
US 2017/0071513 A1   Mar. 16, 2017

Related U.S. Application Data

(60) Provisional application No. 61/993,908, filed on May 15, 2014.

(51) Int. Cl.
*A61B 5/1495* (2006.01)
*A61B 5/145* (2006.01)
*A61B 5/1473* (2006.01)

(52) U.S. Cl.
CPC .......... *A61B 5/1495* (2013.01); *A61B 5/1473* (2013.01); *A61B 5/14532* (2013.01); *A61B 5/14546* (2013.01); *A61B 2560/0223* (2013.01)

(58) Field of Classification Search
CPC ......... A61B 5/145; A61B 5/146; A61B 5/147; A61B 5/148; A61B 5/149
See application file for complete search history.

(56) References Cited

U.S. PATENT DOCUMENTS

2005/0197621 A1* 9/2005 Poulsen ............... A61B 5/0002
604/67
2006/0189863 A1* 8/2006 Peyser ................. A61B 5/0031
600/345
(Continued)

FOREIGN PATENT DOCUMENTS

EP    15793074.4   12/2017
RU    2 244 506 C2   1/2005
(Continued)

OTHER PUBLICATIONS

O'Neal and Jenkins (2010) "Continuous glucose monitoring: comparing real-time and retrospective devices" Infusystems USA 7(4):26-30.
(Continued)

*Primary Examiner* — Meredith Weare
(74) *Attorney, Agent, or Firm* — One LLP

(57) ABSTRACT

Methods, computers, and systems used to improve accuracy of analyte level measurement of an in vivo positioned analyte sensor are disclosed herein. The methods, computers, and systems disclosed herein may be used to provide a calibrated analyte level. Specific embodiments relate to methods, computers, and systems for improving accuracy of glucose measurement of an in vivo positioned glucose sensor.

22 Claims, 6 Drawing Sheets

(56) References Cited

U.S. PATENT DOCUMENTS

| | | | |
|---|---|---|---|
| 2007/0016381 A1 | 1/2007 | Kamath et al. | |
| 2008/0270187 A1* | 10/2008 | Fors | G06Q 50/24 |
| | | | 705/3 |
| 2010/0268477 A1 | 10/2010 | Mueller, Jr. et al. | |
| 2012/0108933 A1 | 5/2012 | Liang | |
| 2012/0191362 A1 | 7/2012 | Schmitt et al. | |
| 2013/0053819 A1* | 2/2013 | Estes | A61M 5/14244 |
| | | | 604/504 |
| 2013/0325352 A1 | 12/2013 | Greene et al. | |
| 2014/0000338 A1 | 1/2014 | Luo et al. | |
| 2015/0241407 A1* | 8/2015 | Ou | A61B 5/14532 |
| | | | 702/19 |

FOREIGN PATENT DOCUMENTS

| | | |
|---|---|---|
| WO | WO 2007/053832 A2 | 5/2007 |
| WO | 2014/035732 | 3/2014 |
| WO | PCT/US15/30880 | 8/2015 |

OTHER PUBLICATIONS

Signal et al. (2012) "Impact of retrospective calibration algorithms on hypoglycemia detection in newborn infants using continuous glucose monitoring" Diabetes technology & therapeutics 14(10):883-890.
RU 2016149127 Office Action, dated Dec. 4, 2018.
AU 2015259020 Examination Report No. 1, dated Jun. 11, 2019.

* cited by examiner

ANALYTE LEVEL CALIBRATION USING BASELINE ANALYTE LEVEL

CROSS-REFERENCE TO RELATED APPLICATION

This application claims priority based on U.S. Provisional Application No. 61/993,908, filed May 15, 2014, the disclosures of which is incorporated by reference herein in its entirety.

INTRODUCTION

In many instances it is desirable to regularly monitor the concentration of particular analytes in body fluid of a subject. A number of systems are available that analyze an analyte in a bodily fluid, such as blood, plasma, serum, interstitial fluid, urine, tears, and saliva. Such systems monitor the level of particular medically relevant analytes, such as, blood sugars, e.g., glucose, cholesterol, ketones, vitamins, proteins, and various metabolites.

In vivo analyte monitoring systems that continuously monitor analyte level include an in vivo positioned analyte sensor. At least a portion of the sensor is positioned beneath the skin surface of a user to contact bodily fluid (e.g., blood or interstitial fluid (ISF)) to monitor one or more analytes in the fluid over a period of time. As such, analyte monitoring is done continuously over a period of time. The sensor may be positioned in the user for a continuous period of time to automatically sense an analyte. Data received or otherwise derived from analyte monitoring may be stored in the analyte monitoring system or communicated to a remote system where it may be stored and/or further processed.

Diagnosis and management of patients suffering from or at risk of developing an abnormal analyte level requires carefully monitoring of analyte level on a daily basis. For example, a patient at risk of developing diabetes mellitus, a disorder of the pancreas where insufficient production of insulin prevents normal regulation of blood glucose level, requires carefully monitoring of blood glucose level on a daily basis. However, the data related to analyte level may need to be calibrated in order to obtain an accurate analyte level.

SUMMARY

Methods, computers, and systems used to improve accuracy of analyte level measurement of an in vivo positioned analyte sensor are disclosed herein. The methods, computers, and systems disclosed herein may be used to provide a calibrated analyte level.

A method of improving accuracy of analyte level measurement of an in vivo positioned analyte sensor is disclosed. Embodiments of the method includes collecting signal data indicative of an analyte level using an in vivo positioned analyte sensor over a period of time; analyzing the collected signal data and identifying signal data points that correspond to a known physiological level for the analyte; and deriving analyte levels from the collected signal data using the identified signal data points as a reference point for the known physiological level of the analyte.

Analyzing the collected signal data to identify signal data points that correspond to a known physiological level for the analyte may include identifying the signal data collected by the sensor at a specified time of the day.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

DETAILED DESCRIPTION

Figure 1:
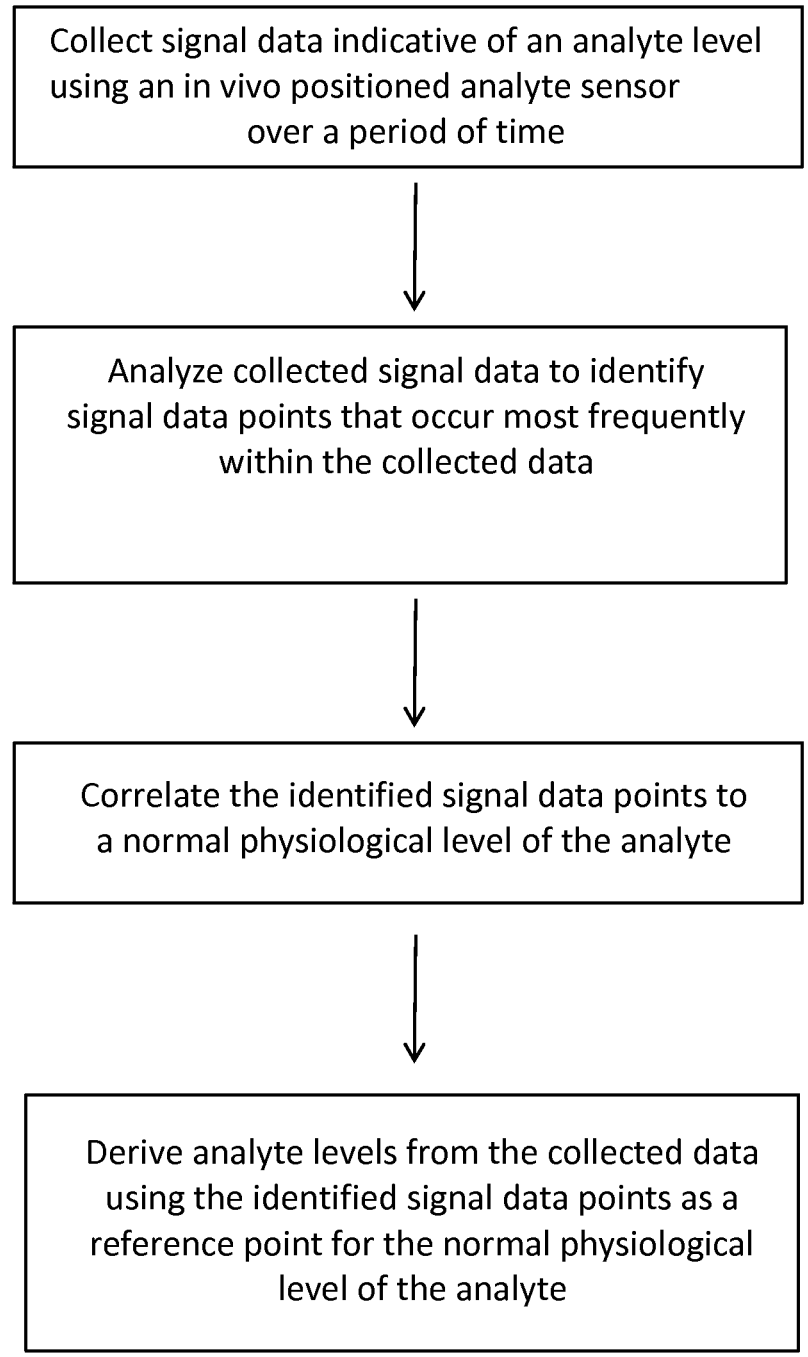
FIG. 1 is a block diagram of an embodiment of a method of improving accuracy of analyte level measurement of an in vivo positioned analyte sensor.

Methods, computers, and systems used to calibrate data related to level of an analyte are disclosed herein. The methods and systems disclosed herein may be used to provide a calibrated analyte level.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a signal data" includes a plurality of such signal data and reference to "the value" includes reference to one or more values and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods of Improving Accuracy of Analyte Level Measurement

In certain embodiments, a method of improving accuracy of analyte level measurement of an in vivo positioned analyte sensor is provided.

The method may include collecting signal data indicative of an analyte level detected by an in vivo positioned analyte sensor; analyzing the collected signal data and identifying signal data points that correspond to a known physiological level for the analyte; and deriving analyte levels from the collected signal data using the identified signal data points as a reference point for the known physiological level of the analyte.

In general, the methods described herein provide an improved accuracy of analyte measurement compared to analyte measurement performed in absence of these methods.

The subject methods may be performed continuously, periodically, retrospectively, or a combination thereof, as described in more detail below.

In certain cases, the methods, sensors, computers, and systems described herein identify signal data points that correspond to a known physiological level for the analyte. A known physiological level for an analyte may be known based on predetermined characteristics of the user in which the in vivo sensor is positioned. For example, the known physiological level for the analyte may be the analyte level that is present in a body fluid of the user at fasting periods, e.g., the levels of the analyte when no food had been consumed by the user in the past 8 hours to 12 hours. In other cases, the known physiological level for the analyte may be the analyte level that is present in a body fluid of the user at a post-meal period. In certain cases, the known analyte level may be a normal physiological level, an above normal level for the analyte or a below normal level.

In certain cases, analyzing the collected signal data and identifying signal data points that correspond to a known physiological level for the analyte may include identifying a period of time of a day for which the physiological level for the analyte is known and identifying the signal data points collected during that period of time and deriving analyte levels from the collected signal data using the identified signal data points as a reference point for the known physiological level of the analyte. For example, once the period of time of the day for which the physiological analyte level is known is identified, the signal data collected during this time period may be correlated to that known analyte level and the remaining signal data may then be converted into analyte levels using a correction factor determined based on the correlation between signal data for that period of time and the known physiological analyte level for that period of time.

In exemplary cases, the known physiological level may be derived from analysis of the collected signal data to identify signal data points that occur most frequently within the collected data. In this embodiment, the identified signal data points may be correlated to a normal physiological level of the analyte. As such, the method may include collecting signal data indicative of an analyte level using an in vivo positioned analyte sensor over a period of time; analyzing the collected signal data to identify signal data points that occur most frequently within the collected data; correlating the identified signal data points to a normal physiological level of the analyte; and deriving analyte levels from the collected data using the identified signal data points as a reference point for the normal physiological level of the analyte. An embodiment of the subject method is depicted in FIG. 1.

As explained herein, the methods, computers, and systems identify signal data points that occur most frequently within the collected data. In certain embodiments, the signal data points that occur most frequently within the collected data serve as a reference point for the normal physiological level of the analyte.

In general, the body tries to maintain a normal physiological level of an analyte. Although the level of an analyte may fluctuate at certain times of the day due to a variety of reasons, in general, the body brings the analyte level back to a normal physiological level. As such, within a certain time period, although fluctuations in an analyte level may occur, during a majority of the time period, the analyte level is present at a normal physiological level. When signal data indicative of an analyte level is measured continuously using an in vivo positioned continuous analyte sensor over a period of time, the signal data may include signal data points that occur most frequently within that period of time. These most frequently occurring signal data points correspond to the signal for the normal physiological level of the analyte. As such, this signal may be used as a reference point for deriving analyte levels. In other words, the signal data may be calibrated using the identified signal data points as a reference point for the normal physiological level of the analyte.

For example, a functioning pancreas will achieve physiological glucose concentration target values of about 90 mg/dL to about 100 mg/dL, e.g., 95 mg/dL by releasing appropriate amount of hormones. Therefore, the collected signal data indicative of glucose level would include a majority of signal data points that correspond to a glucose level of 95 mg/dL ($\pm$1%-5%). Identification of the signals that correspond to a glucose level of 95 mg/dL ($\pm$1%-5%) will in turn provide the reference point which can be used to derive glucose level from the other signal data points and accurately identify times of the day when the glucose levels are above or below the normal physiological level. Accordingly, the subject methods, computers and systems are useful for improving accuracy of measurement of analyte level.

In certain cases, the continuous analyte sensor may be a continuous glucose sensor and may be positioned in a subject. The subject may be: a healthy subject, a subject who is at risk of developing diabetes, a pre-diabetic, or an early stage of diabetes. In certain cases, the continuous glucose sensor may be positioned in a patient having or suspected of having impaired glucose tolerance or non-insulin dependent type 2 diabetes. In certain cases, the subject may be an obese subject, a subject having high blood pressure, and/or high triglyceride levels.

Figure 2:
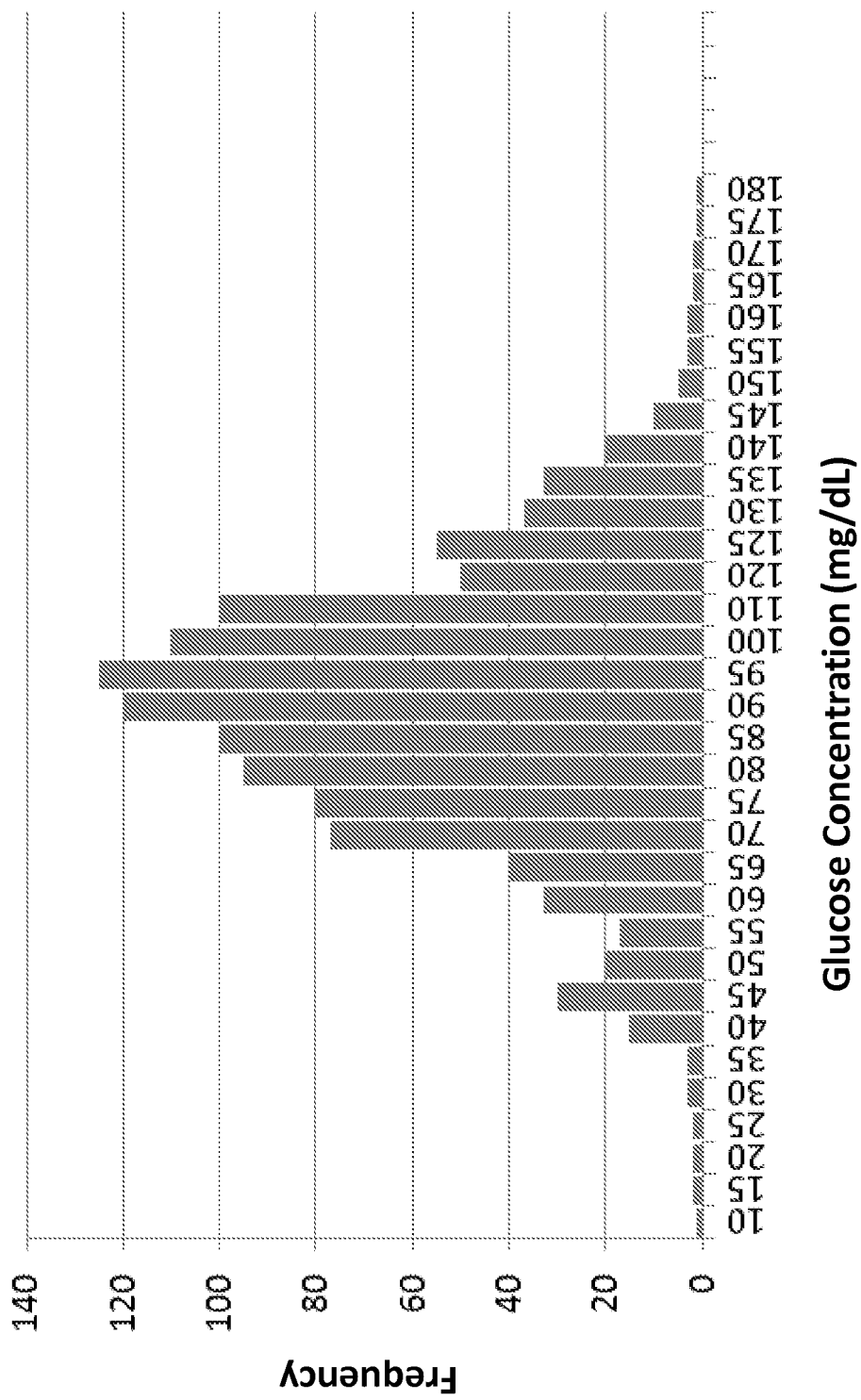
FIG. 2 is a histogram of blood glucose values in a subject with impaired glucose tolerance.

An exemplary glucose concentration histogram of a subject who may be pre-diabetic or may have impaired glucose tolerance or non-insulin dependent type 2 diabetes is depicted in FIG. 2. FIG. 2 shows that the person may have higher than normal plasma glucose levels at certain times during the day but mostly the glucose level stays within the normal glucose range. The graph in FIG. 2 illustrates that the majority of a time, the body maintains a glucose level within a normal range. As shown in FIG. 2, a glucose concentration of around 95±5% mg/dL is present most frequently as compared to glucose concentrations outside of the 95±5% mg/dL range. As such, the signal value that occurs most frequently in the measured signal data corresponds to a normal physiological range in a person whose glucose is regulated normally or regulated to some extent by the body. Therefore, in a healthy subject, who does not have a glucose metabolism related disorder, the blood glucose levels corresponds to a normal physiological range during the majority of the day. Similarly, in a person who is pre-diabetic or has impaired glucose tolerance or non-insulin dependent type 2 diabetes, although the blood glucose value may fluctuate to a greater extent (as compared to a healthy person), the body is still able to maintain glucose homeostasis. Therefore, in a pre-diabetic person or in a person who has impaired glucose tolerance or non-insulin dependent type 2 diabetes, the blood glucose level corresponds to a normal physiological range during the majority of the day. In contrast, in patients with type 1 diabetes this is not the case. Specifically, in patients with type 1 diabetes, the blood glucose level does not correspond to a normal physiological range during the majority of the day.

In certain cases, the methods, computers and systems described herein may be used to monitor blood glucose levels in a subject whose glucose is regulated to some extent by the body, such as a healthy subject, or a subject who is at risk of developing diabetes, is a pre-diabetic, or is an early stage of diabetes, has or is suspected of having impaired glucose tolerance, or non-insulin dependent type 2 diabetes.

In certain cases, the subject method, computers and systems may not be used to derive glucose level in a subject who has type 1 diabetes. In certain cases, the signal data indicative of glucose level, collected using an in vivo glucose sensor positioned in a person with type 1 diabetes, may be analyzed to identify signal data points that occur most frequently within the collected data. As noted above, in a person having type 1 diabetes, signal data points that occur most frequently within the collected data may not be identified. The collected data may be calibrated using a different method, such as, a method that involves measuring blood glucose using test strips or sensor factory calibration.

In certain cases, collecting signal data indicative of an analyte level using an in vivo positioned analyte over a period of time may include recording of the signal data. In certain embodiments, the recorded data may be stored in the memory of a device. The device may be physically integrated with the in vivo continuous analyte sensor. For example, the in vivo continuous analyte sensor may be present in a housing that also includes memory for storing the collected signal data. In addition or alternatively, the in vivo continuous analyte sensor may transmit the signal data to a remote device that includes a memory for storing the collected data. For example, the in vivo continuous analyte sensor may communicate (e.g., wired or wirelessly) with a remote device, where the remote device may download the signal data continuously or intermittently.

The remote device may be, for example, data processing device such as a personal computer, laptop, cell phone or smartphone, personal digital assistant (PDA), an analyte monitoring device, such as any variety of hand-held measurement instruments or analysis instruments, such as a blood glucose meter or reader. For example, glucose related signal may be measured by in vivo positioned glucose sensor and recorded in memory of the sensor electronics and/or sent to a remote device such as a receiving unit, e.g., a processing device, such as, a computer or a glucose monitoring device.

In some aspects, the methods, devices, and systems relate to devices and systems including an in-vivo positioned analyte sensor that may be configured so that at least a portion thereof is placed under the skin of the patient to detect the analyte levels of the patient, and another portion of the analyte sensor—which may be above the skin—is coupled to electronics within a housing that is positioned externally on the skin of the subject. The sensor electronics may include various components, such as communication element(s) for communication with a remote receiving unit; a processor; memory; etc.

The recorded signal data may then be analyzed by a signal data processing algorithm in the processor of a device, such as, the in vivo positioned analyte sensor or another device that collects/receives the signal data. In certain cases, the device that collects/receives the signal data may collect/receive a raw signal data collected by the in vivo positioned sensor. In other cases, the device that collects/receives the signal data may collect/receive a signal data that has been processed by the in vivo positioned sensor or another intermediate device that received the raw signal data from the in vivo positioned sensor.

In certain cases, the period of time over which the signal data indicative of an analyte level using an in vivo positioned analyte is collected may range from 6 months to 1 day, e.g., 5 months, 4 months, 3 months, 2 months, 1 months, 4 weeks, 3 weeks, 2 weeks, 1 week, 6 days, 5 days, 4 days, 3 days, 2 days, or 1 day. The signal data may be data collected every minute, every 5 minutes, every 10 minutes, every 15 minutes, every 20 minutes, every 25 minutes, or every 30 minutes during the period of time.

In certain cases, analyzing the collected signal data may include analyzing a subset of the collected signal data corresponding to a subset of the period of time during which the data was collected to identify signal data points that occur most frequently within the subset of collected data. As such, analyzing the collected signal data may include analyzing a subset of the collected data. For example, the collected data may be data collected every minute, every 5 minutes, every 10 minutes, every 15 minutes, every 30 minutes, every hour, every 2 hours, or every 3 hours, or every 5 hours, over a period of time of 1 day, 2 days, 3 days, 4 days, 5 days, 6 days, 7 days, 14 days, 21 days, 30 days, or more. A subset of the collected data may be analyzed. In certain embodiments, the subset may be data collected over a period of time of 6 hours, 12 hours, or 16 hours from a collected signal data that spans 1 day, 2 days, 3 days, 4 days, 5 days, 6 days, 7 days, 14 days, 21 days, 30 days, or more days. In certain embodiments, the subset may be data collected over a period of 12 hours, 16 hours, 18 hours, 24 hours or 48 hours from a collected signal data that spans 3 days, 4 days, 5 days, 6 days, 7 days, 14 days, 21 days, 30 days, or more days. As noted above, the signal data may be data collected every minute, every 5 minutes, every 10 minutes, every 15 minutes, every 20 minutes, every 25 minutes, or every 30 minutes during the period of time.

The subset of the collected signal data corresponding to a subset of the period of time may be analyzed to identify signal data points that occur most frequently within the subset of collected data.

Numerous methods for identifying most frequently occurring numbers in a set of numbers are known. Such methods may be utilized to identify the signal data points that occur most frequently within the subset of collected data. Exemplary methods for determining most frequently occurring numbers include statistical methods such as, kernel density estimation (KDE), mode determination, graphical methods, such as, bell curve, Gaussian curve, histogram, dot plot, and the like.

In certain instances, the most frequently occurring signal data points may be identified by calculating the mode of the collected signal data being analyzed, e.g. a subset of the collected signal data. In certain cases, determining the mode of the subset of the collected signal data may include creating a frequency distribution of the subset of the collected signal data.

In certain cases, a graph, such as, a histogram may be created for determining the most frequently occurring signal data points within the data being analyzed. In certain cases, a histogram may be created by plotting on the X-axis, the collected signal data being analyzed and on the Y-axis, the number of times a particular signal data point occurs in the collected signal data being analyzed. The most frequently occurring signal data will be present at the highest peak of the histogram and will be identified as the signal data point that occurs most frequently within the collected data as compared to the other signals present in the collected data. As noted above, the identified signal data points correspond to the signal indicative of normal physiological level of the analyte and therefore serve as the reference point for the normal physiological level of the analyte.

In one example, the analyte may be glucose and the measured signal data may be current and the following signals may be measured in nanoAmperes (nA) 5, 6, 7, 8, 9, 10, 10, 10, 10, 10.4, 10.6, 10.8, 11, 12. In this case, 10 nA may be identified as the most frequently occurring data point which corresponds to a normal physiological level of 95 mg/dL. In this example, the 10 nA may then be used as a reference point to derive glucose level from the remaining collected data.

In other embodiments, signal data points that differ by ±1% to ±5% are considered to be within the same range or bin. For example, if the measured signal is current and the measured signals are, for example, 4.1, 4.2, 4.3, 4.4, 4.5, and 4.6, the signals 4.1-4.4 can each be considered to be a signal within a single range or bin and can be counted as four occurrences of signal points in this bin and signals 4.5 and 4.6 can be considered to be signals within another single range or bin and counted as two occurrences of signal points in this bin. In another example, the following signals are measured in nanoAmperes (nA) 5, 5.2, 5.8, 6, 6.3, 6.5, 7, 8, 9, 9.4, 9.8, 10, 10.1, 10.2, 10.3, 10.4, 10.5, 10.6, 10.8, 11, 12. Current values in the range of 5 to less than 5.5 may be considered to be in a single bin and the number of occurrences of signal data points that fall within this bin may be determined. Similarly, additional data point ranges/bins may include ranges of 5.5 to less than 6, 6 to less than 6.5, 6.5 to less than 7, 7 to less than 7.5, 7.5 to less than 8, 8 to less than 8.5, 8.5 to less than 9, 9 to less than 9.5, 9.5 to less than 10, 10 to less than 10.5, 10.5 to less than 11, 11 to less than 11.5, 11.5 to less than 12, 12 to less than 12.5. Signal data points may be placed in each of such a data range/bin and the frequency of occurrence of these data points may be noted. In this example, current values in the range of 10, 10.1, 10.2, 10.3, 10.4 are treated counted as five occurrences in the range/bin of 10 to less than 10.5 and are determined to be the most frequently occurring signal data points. In this example, the signal data points that range from 10 to less than 10.5 nA may be used as the data points that correspond to the signals indicative of normal physiological level of the analyte and therefore serve as the reference point for the normal physiological level of the analyte. For example, the data points in the range of 10 to less than 10.5 nA may correspond to a normal physiological level of 95 mg/dL glucose. The remaining current values measured may then be calibrated accordingly.

As noted above, in certain cases, a subset of the collected data may be analyzed. In certain cases, if no mode is identified from the subset of the collected signal data, for example a first subset, the method may include analyzing another subset of the collected signal data, for example a second subset.

In certain cases, the first subset of the collected signal data may differ from the second subset. For example, the second subset of the collected signal data may correspond to a second subset of the period of time over which the signal data is collected. In certain embodiments, the second subset of period of time may be longer than the first subset of period of time over which the signal data is collected, where the first subset of collected signal data corresponds to the first subset of period of time. The first and second subset of period of time may or may not overlap.

In certain cases, the collected signal data may first be scanned to identify a subset of the collected data for analysis. For example, a period of time during which the collected signal data is relatively stable may be selected and the data collected during this period of time may be analyzed.

In certain cases, the subset of period of time (time during which the subset of signal data that is analyzed was collected) may be an early morning time, for example between 4 AM-7 AM, e.g., 4:30 AM-7 AM; 5 AM-7 AM; 5:30 AM-7 AM; 6 AM 7 AM; 5 AM-7 AM; or 5:30 AM-7 AM. In certain cases, the subset of period of time may be the time between at least 8 hours post consumption of food and before consumption of food. In certain cases, the subset of collected signal data that is analyzed to identify the most frequently occurring data points may be a plurality of subset of data collected at a same time of the day, such as, the time corresponding to at least 8 hours post consumption of food.

In certain cases, the subset of data that is used to identify the most frequently occurring data points and hence the data points that correspond to a normal physiological analyte level may be the data collected on the first day, the first two days, the first three days, the first five days, the first six days, or the first seven days of positioning the analyte sensor in a subject. The data points identified as corresponding to a normal physiological analyte level may then be used to calibrate or derive the signal data points collected during the entire time the sensor was positioned in the subject.

Figure 3A:
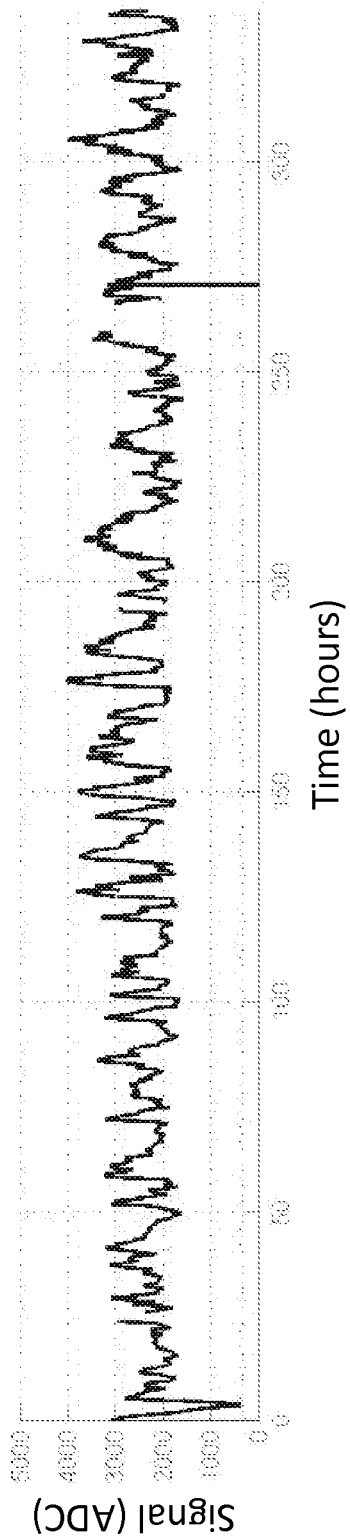
FIGS. 3A and 3B are raw glucose related signal data collected over a period of about 350 hours.
Figure 3B:
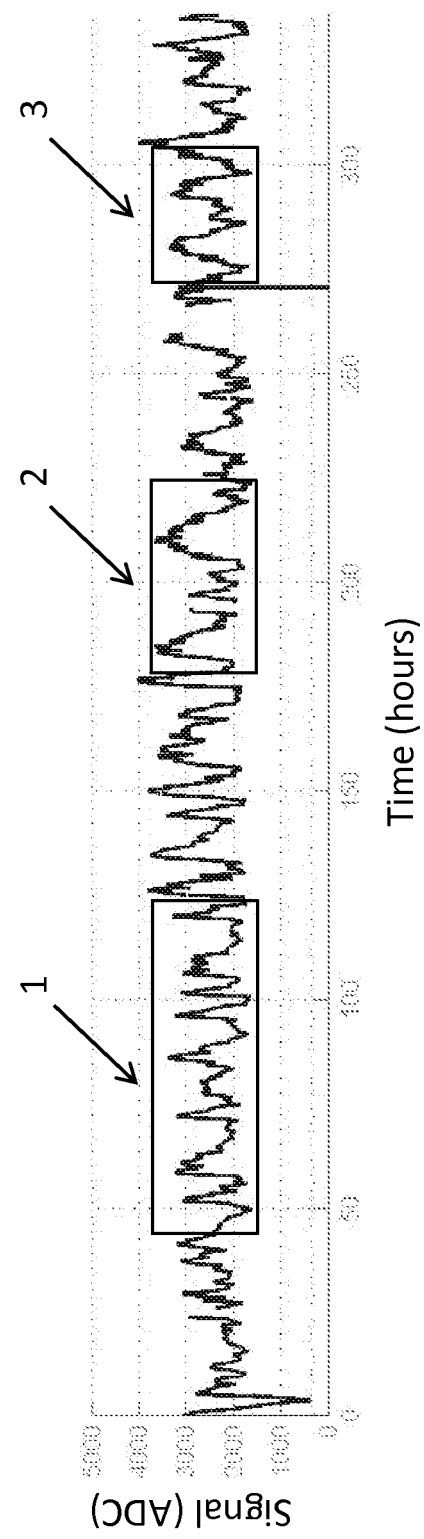

In certain embodiments, analyzing a subset of the collected signal data corresponding to a subset of period of time to identify signal data points that occur most frequently within the subset of collected data may include scanning the collected signal data and selecting a window of time where the signal data is stable. An example of signal data measured using an in vivo glucose sensor positioned in a subject suspected of having a pre-diabetic condition is depicted in FIG. 3. FIGS. 3A and 3B depict the glucose related signal recorded over a time period of 350 hours. The glucose related signal is reported in an arbitrary unit of analyte to digital count (ADC). In this example, the subset of period of time that may be selected may be one or more of the following time periods as depicted in FIG. 3B: about 45 hr to about 125 hrs (window 1); about 175 hrs to about 225 hrs (window 2); and about 275 hrs to about 305 hr (window 3), while the data collected over the subset of period of time corresponding to the following time periods: about 0 hrs to about 44 hrs; about 126 hrs to about 174 hrs; and about 226 hrs to about 274 hrs may not be selected for analysis. The most frequently occurring signal data points may then be identified within a selected subset of the collected data by methods described here or other methods for identifying most frequently occurring data point.

In other embodiments of the subject method, the entire glucose related signal collected from an individual may be used for identifying the most frequently occurring signal data points.

In yet other embodiments, glucose related signal collected from an individual over a period of several weeks, such as, 4 weeks, 3 weeks, 2 weeks may be used for identifying the most frequently occurring signal data points.

In other embodiments, glucose related signal collected from an individual over a period of several days, such as, 10 days, 7 days, 6 days, 5 days, 4 days, 3 days, or 2 days may be used for identifying the most frequently occurring signal data points.

In other embodiments, glucose related signal collected from an individual over a period of several hours, such as, 42 hrs, 40 hrs, 36 hrs, 35 hrs, 30 hrs, 24 hrs, 18 hrs, 16 hrs, 12 hrs, or less may be used for identifying the most frequently occurring signal data points.

Correlating the identified signal data points to a normal physiological level of the analyte may include assigning the most frequently occurring signal data points a glucose concentration value of 90 mg/dL-100 mg/dL, e.g., 95 mg/dL (±1% to 5%). In certain embodiments, correlating the identified signal data points to a normal physiological level of the analyte may include calculating a calibration factor from the identified signal data points. The calibration factor can be determined by dividing the normal blood glucose concentration (BGnormal, e.g., 95 mg/dL) by the most frequently occurring sensor signal (Sf). The glucose values for all data points (BG) can then be calculated as:

BG=Sensor Signal*(BGnormal/$S\!f$)

In certain cases, deriving analyte levels from the collected data using the identified signal data points as a reference point for the normal physiological level of the analyte may include calculating the analyte concentration from the remaining signal data points by using a formula that assigns the normal physiological analyte concentration to the most frequently occurring data points. For example, if the most frequently occurring sensor signal is 10 nA (±1% to 5%) and the normal physiological glucose concentration is 95 mg/dl, the glucose concentration for all time points can be calculated from the sensor signal as:

Glucose=Sensor Signal*(95/10)

In the above example, the most frequently occurring sensor signal of 10 nA may be derived by calculating a mean of the sensor signal data points that are in the range of 10 to less than 10.5 nA.

In certain cases, as explained herein, a subset of collected signal data corresponding to a subset of the period of time may be analyzed to identify signal data points that occur most frequently within the subset of collected data and correlating the identified signal data points to a normal physiological level of the analyte. In such a case, the identified signal data points may be used as a reference point for the normal physiological level of the analyte for deriving analyte levels from the collected data, where the entire collected data is derived or only a subset of the collected data is derived. In other words, the calibration may be applied to the entire collected data or to a subset of the collected data.

In certain cases, deriving analyte levels from the collected data using the identified signal data points as a reference point for the normal physiological level of the analyte may include additionally using a factory calibration factor for the in vivo analyte sensor. For example, the collected data may be calibrated using a calibration factor derived from the correlation of the identified signal data points to a normal physiological level of the analyte. In addition, the collected data may be calibrated using the factory calibration factor following the manufacturer's instructions.

In certain cases, if no signal data points are identified as the most frequently occurring data points, then the collected signal data may only be calibrated using the factory calibration factor.

In certain cases, the collected data may be calibrated using a calibration factor derived from the correlation of the identified signal data points to a normal physiological level of the analyte. In addition, the collected data may be calibrated using analyte measurement performed using a test strip or a laboratory instrument.

As such, in certain embodiments, the collected data may be derived into analyte levels by factoring in a calibration factor calculated using the most frequently occurring signal data points and optionally by using a calibration factor calculated by measuring the analyte concentration by an alternate device, such as, analyte test strip or a laboratory instrument.

Similarly, in certain embodiments, the collected data may be derived into analyte levels by factoring in a calibration factor calculated using the most frequently occurring signal data points and optionally by using a factory calibration factor determined for a batch of in vivo analyte sensors.

As used herein, most frequently occurring signal data points refer to data points that occur more frequently than any other data points are in the data being analyzed. In general, as explained in detail herein, signal data points within ±1%-±5% range of each other are considered to be in the same range and each occurrence of such data points are counted separately; the number of occurrences of the data points in the same range is counted and compared to number of occurrences of data points in other ranges to identify the data points that are most commonly present.

In general, signal data points that occur most frequently within the analyzed data, occur at least 1.1 times more often than other signal data points in the analyzed data. In general, signal data points in the analyzed data are grouped into ranges or bins where data points within ±1%-±5% of each other placed in the same bin/range. In general, when the number of occurrences of the data points in a first bin is at least 1.1 times higher than the number of occurrences of the data points in any of the other bins, the first bin may be identified as the most frequently occurring bin and as the data points within that first bin may be identified as the most frequently occurring data points and used as a reference point for the normal physiological level of the analyte.

In certain cases, signal data points that occur most frequently within the collected data being analyzed may be above a frequency threshold. In certain cases, the frequency threshold may be the percent of data that is represented by the most frequently occurring data. In certain cases, the frequency threshold may be about 5%. For example, the frequency threshold may be at least 4%, 5%, 6%, 7%, 8%, 9%, 10%, 12%, 15%, 20%, 25%, 30%, 35%, 40%, 50%, 55%, 60%, or 70% or more. As such, a signal data range that occurs most frequently within the data being analyzed and make up at least 5% of the analyzed data is identified as occurring most frequently within the analyzed data. For example, in certain cases, when the most frequently occurring signal data is in the range of 10 nA—less than 10.5 nA, signals that are present within this range may be considered to be above a frequency threshold when they make up at least 5% of the signals in the collected data being analyzed.

In certain cases, signal data points that occur most frequently within the collected data being analyzed may be above a relative frequency threshold. In certain cases, the relative frequency threshold may be 1.1 times (1.1×) or more, where a data range is identified as the most frequently occurring data range when the data points within the data range occur at least 1.1 times more than in any of the other data ranges in the analyzed data. For example, the relative frequency threshold may be 1.2×, 1.3×, 1.4×, 1.5×, 1.6×, 1.7×, 1.8×, 1.9×, 2×, or more than any of the other data ranges in the analyzed data. For example, if the data points in the data range of 10 nA-less than 10.5 nA occur most frequently and occur at least 1.1 times more than the number of occurrences of the data points in any other data range in the analyzed data, the data range may be identified as the most frequently occurring data range. In certain cases, the relative frequency threshold may be at least 2×, 3×, 4×, or higher.

In certain cases, signal data points that occur most frequently within the collected data may not be identified. For example, the analyzing the collected signal data to identify signal data points that occur most frequently within the collected data may not reveal signal data points that occur most frequently within the collected data, and/or are above a relative frequency threshold of 1.1 and optionally, are above a frequency threshold of 4%.

As noted above, if a most frequently occurring signal range is not identified, the collected data may be derived using a predetermined calibration factor, such as, a factory set calibration factor to provide improved analyte measurement.

In certain cases, the in vivo analyte sensor may be positioned in a person without physiological glucose regulation (e.g. type 1 diabetes). The methods, computers and systems described herein may analyze signal data indicative of an analyte level collected using an in vivo positioned analyte sensor over a period of time. The analyzing the collected signal data to identify signal data points that occur most frequently within the collected data or a subset thereof may include determining the most frequently occurring data points that occur at least 1.1 times more often than any of the other data points in the collected data being analyzed.

In the case of a person with type 1 diabetes, no signal data points that occur most frequently may be identified. In such as case, the methods, computers and systems described herein calibrate the collected data using a predetermined calibration factor, such as, a factory designated calibration factor.

In general, the signal data indicative of an analyte level detected by an in vivo positioned analyte sensor is signal generated from electrolysis of the analyte present in the body fluid at the location at which the sensor is positioned. This signal data may be the raw data generated from the electrolysis or may be processed data, e.g., raw data that has been converted into a logarithmic data, analog data, or the like. Signal data may be voltage, current, resistance, capacitance, charge, conductivity, or a combination thereof.

In general, analyte level refers to concentration of the analyte in a body fluid. Analyte levels are generally obtained from signal data indicative of the level of the analyte. The signal data is converted to analyte levels expressed in units such as, Molar (M), mol/L, mg/dL, and the like.

In exemplary embodiments, the method for improving accuracy of an analyte level may be carried out continuously, such as, in real time—the collected signal data may be continuously analyzed and analyte levels derived therefrom. In other cases, the method for improving accuracy of an analyte level may be carried out periodically, for example, the collected signal data may be analyzed and analyte levels derived therefrom every 1 hour, 2 hours, 4 hours, 6 hours, 10 hours, 16 hours, 24 hours, 48 hours. In certain cases, the method for improving accuracy of an analyte level may be carried out retrospectively, such as, after the signal data has been collected from the in vivo analyte sensor and the data is being analyzed to provide a diagnosis for a patient.

Computers and Systems for Improving Accuracy of Analyte Measurement

Also disclosed herein are computers and systems for improving analyte measurement of an in vivo positioned analyte sensor. In certain embodiments, the computer may include a memory and a processor, the memory operably coupled to the processor, wherein the memory comprises instructions stored therein to be executed by the processor.

In certain embodiments, the instructions may include instructions for collecting signal data indicative of an analyte level detected by an in vivo positioned analyte sensor; analyzing the collected signal data and identifying signal data points that correspond to a known physiological level for the analyte; and deriving analyte levels from the collected signal data using the identified signal data points as a reference point for the known physiological level of the analyte.

In certain embodiments, the instructions may include instructions for collecting signal data indicative of an analyte level using an in vivo positioned analyte sensor over a period of time; analyzing a subset of the collected signal data corresponding to a subset of the period of time to identify signal data points that occur most frequently within the subset of collected data; correlating the identified signal data points to a normal physiological level of the analyte; and deriving analyte levels from the collected data using the identified signal data points as a reference point for the normal physiological level of the analyte.

Figure 4:
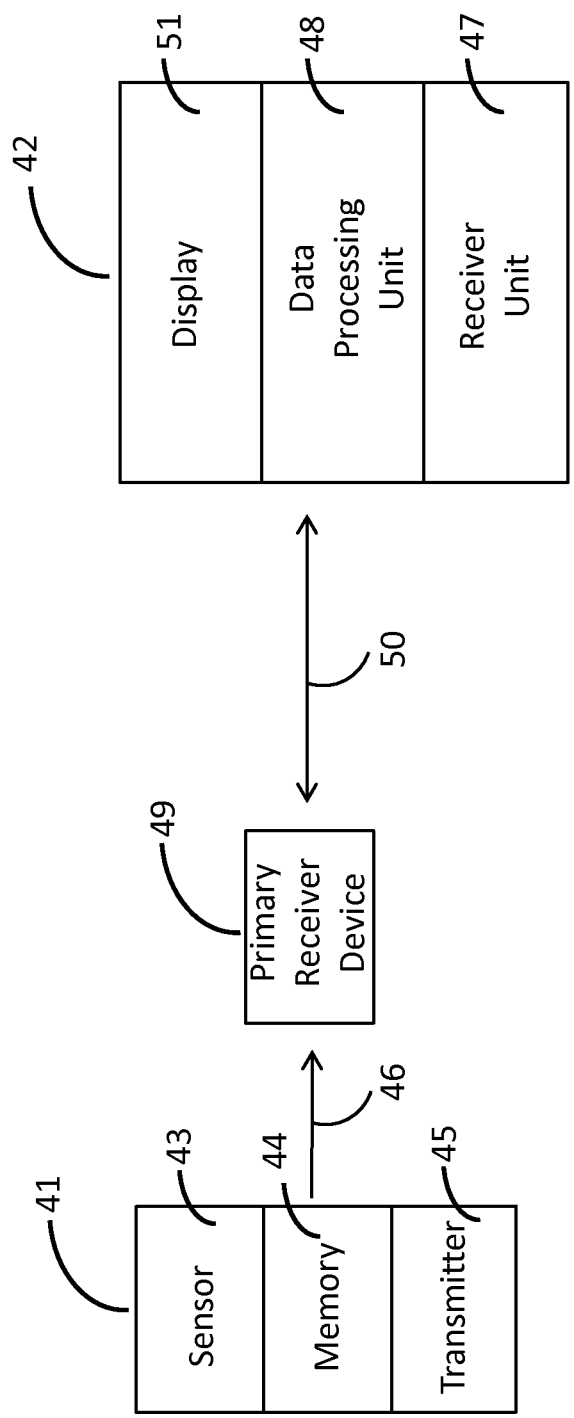
FIG. 4 depicts an exemplary system of the present disclosure.

Systems for improving analyte measurement of an in vivo positioned analyte sensor may include a computer as described herein and an in vivo positioned analyte sensor. FIG. 4 depicts an exemplary system 40 that may be used to improve analyte measurement of an in vivo positioned analyte sensor 41. As shown in FIG. 4, the system 40 includes the in vivo positioned analyte sensor unit 41 and a computer 42. The in vivo positioned analyte sensor unit 41 may include a sensor 43, a memory 44 for storing the collected signal data and/or a transmitter 45 for transmitting the data over a communication link 46 to the computer 42 either directly or via a primary receiver device 49. The computer 42 includes a receiver unit 47 for receiving the collected signal data either from the transmitter 45 or from primary receiver device 49. The primary receiver device 49 may transmit the collected data over the communication link 50. The receiver unit 47 may also include a data processing unit 48 or the receiver unit 47 may be operably linked to a data processing unit 48 within the computer 42. The computer may additionally include a display 51 to display the collected signal data, calibration factor(s), calibrated signal data, and/or derived analyte levels. The data processing unit may transmit the derived analyte levels to the primary receiver device over the communication link 50. In vivo positioned analyte sensor units are further described below.

The instructions may include the instructions for performing the methods described herein.

In certain cases, the memory comprising the instructions for performing the subject methods and the processor operably coupled to the processor may part of the in vivo positioned analyte sensor and may be physically connected to the in vivo positioned analyte sensor. For example, the memory and processor may be present in the on skin portion of the in vivo analyte sensor. In certain embodiments, the in vivo analyte sensor may function as a self-calibrating analyte sensor that continuously or retrospectively calibrates the signal data related to analyte levels collected by the sensor. As described herein, the calibrated of the collected signal data may be performed using the methods for improving analyte measurement of an in vivo positioned analyte sensor as described herein.

Electrochemical Sensors

Embodiments of the present disclosure relate to methods and devices for detecting at least one analyte, including glucose, in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time. Embodiments include combined or combinable devices, systems and methods and/or transferring data between an in vivo continuous system and a device that includes a memory operably connected to a processor.

Embodiments include wholly implantable analyte sensors and analyte sensors in which only a portion of the sensor is positioned under the skin and a portion of the sensor resides above the skin, e.g., for contact to a sensor control unit (which may include a transmitter), a receiver/display unit, transceiver, or processor, etc. The sensor may be, for example, subcutaneously positionable in a user for the continuous or periodic monitoring of a level of an analyte in the user's interstitial fluid. For the purposes of this description, continuous monitoring and periodic monitoring will be used interchangeably, unless noted otherwise.

Analyte sensors may be insertable into a vein, artery, or other portion of the body containing fluid. Embodiments of the analyte sensors may be configured for monitoring the level of the analyte over a time period which may range from seconds, minutes, hours, days, weeks, to months, or longer.

In certain embodiments, the analyte sensors, such as glucose sensors, are capable of in vivo detection of an analyte for one hour or more, e.g., a few hours or more, e.g., a few days or more, e.g., three or more days, e.g., five days or more, e.g., seven days or more, e.g., several weeks or more, or one month or more. Future analyte levels may be predicted based on information obtained, e.g., the current analyte level at time $t_0$, the rate of change of the analyte, etc.

In an electrochemical embodiment, the sensor is placed, transcutaneously, for example, into a subcutaneous site such that subcutaneous fluid of the site comes into contact with the sensor. In other in vivo embodiments, placement of at least a portion of the sensor may be in a blood vessel. The sensor operates to electrolyze an analyte of interest in the subcutaneous fluid or blood such that a signal (e.g., current) is generated between the working electrode and the counter electrode. A value for the current associated with the working electrode is determined. If multiple working electrodes are used, current values from each of the working electrodes may be determined. A microprocessor may be used to collect these periodically measured current values or to further process these values.

In certain embodiments, the periodically measured analyte related signal may be displayed, stored, transmitted, and/or otherwise processed to provide useful information. By way of example, raw signal may be used as a basis for determining analyte concentration during a period of 24 hrs and/or a rate of change in analyte concentration, which should not change at a rate greater than a predetermined threshold amount. If the rate of change of analyte concentration exceeds the predefined threshold, an indication maybe displayed or otherwise transmitted to indicate this fact.

As demonstrated herein, the methods of the present disclosure are useful in connection with a device that is used to measure or monitor an analyte (e.g., glucose), such as any such device described herein. These methods may also be used in connection with a device that is used to measure or monitor another analyte (e.g., ketones, ketone bodies, HbA1c, and the like), including oxygen, carbon dioxide, proteins, drugs, or another moiety of interest, for example, or any combination thereof, found in bodily fluid, including subcutaneous fluid, dermal fluid (sweat, tears, and the like), interstitial fluid, or other bodily fluid of interest, for example, or any combination thereof. In general, the device is in contact, such as thorough and substantially continuous contact, with the bodily fluid.

According to embodiments of the present disclosure, the measurement sensor is one suited for electrochemical measurement of analyte concentration, for example glucose concentration, in a bodily fluid. In these embodiments, the measurement sensor includes at least a working electrode and a counter electrode. Other embodiments may further include a reference electrode. The working electrode is typically associated with an analyte-responsive enzyme. A mediator may also be included. In certain embodiments, hydrogen peroxide, which may be characterized as a mediator, is produced by a reaction of the sensor and may be used to infer the concentration of glucose. In some embodiments, a mediator is added to the sensor by a manufacturer, i.e., is included with the sensor prior to use. The redox mediator may be disposed relative to the working electrode and is capable of transferring electrons between a compound and a working electrode, either directly or indirectly. The redox mediator may be, for example, immobilized on the working electrode, e.g., entrapped on a surface or chemically bound to a surface.

Analytes that may be monitored include, but are not limited to, acetyl choline, amylase, bilirubin, cholesterol, beta hydroxy butyrate, chorionic gonadotropin, glycosylated hemoglobin (HbA1c), creatine kinase (e.g., CK-MB), creatine, creatinine, fructosamine, glucose, glucose derivatives, glutamine, hormones, growth hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

An in vivo analyte sensor unit may include the electronic components that operate the sensor, the memory, and the transmitter. The electronic components of the sensor unit typically include a power supply for operating the sensor, the memory, and the transmitter. The electronic components of the sensor unit also includes a sensor circuit for obtaining signals from and operating the sensor, a processing circuit that obtains signals from the sensor circuit and provides the signals to a memory and/or a transmitter. In some embodiments, the processing circuit may include digital logic circuitry.

The sensor unit may optionally contain a transmitter for transmitting the sensor signal data from the processing circuit to a receiver unit, a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor unit may also include digital and/or analog components utilizing semiconductor devices, including transistors. To operate these semiconductor devices, the sensor unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the processing circuit. The processing circuit relays the raw signals to a memory and/or transmitter which in turn may communicate the raw signal data to a computer.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Calibration of Glucose Sensor Data

Figure 5A:
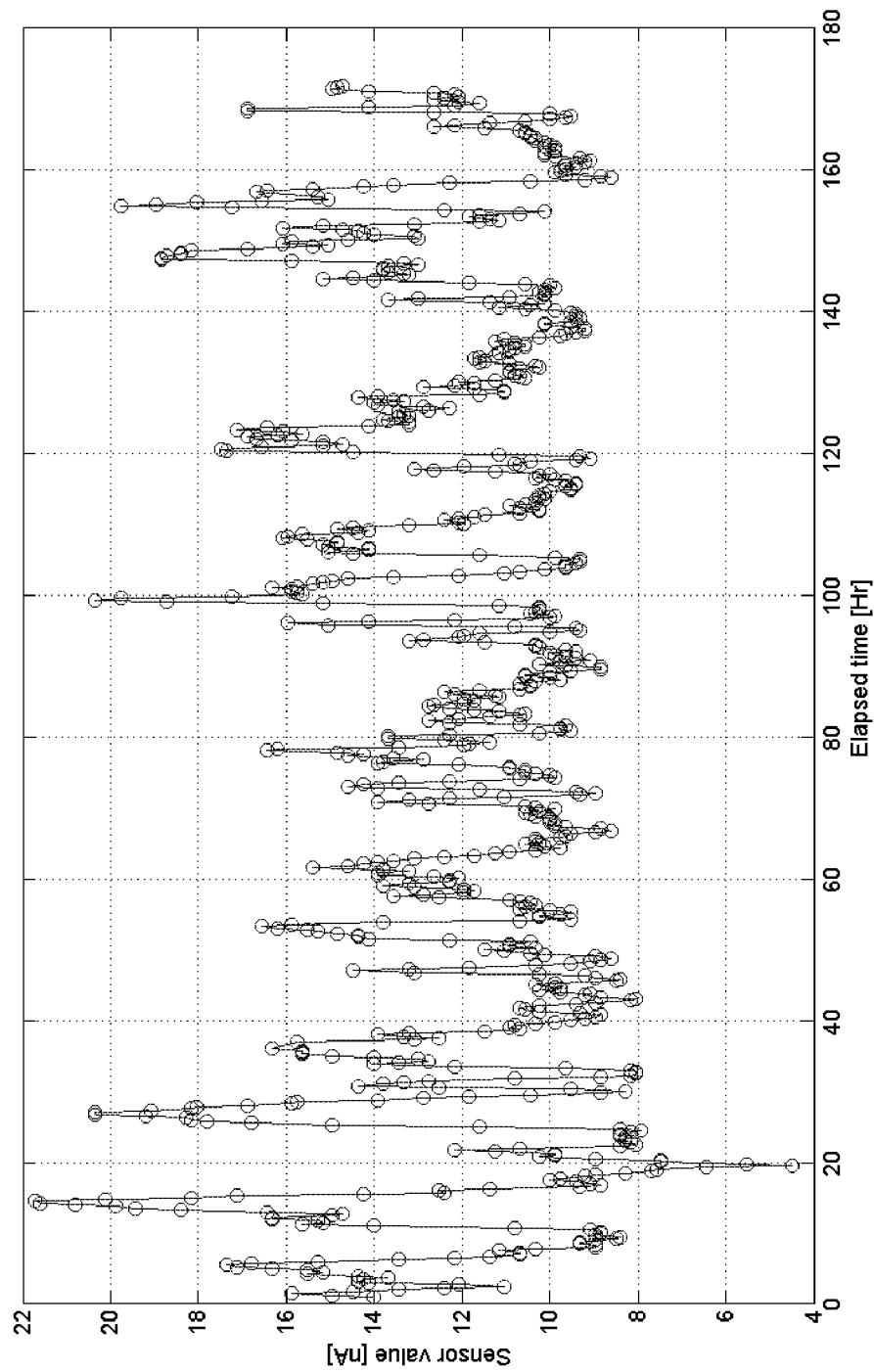
FIG. 5A is a graph of glucose related current collected over a period of about 180 hours.

Glucose related signal data was measured by an in vivo positioned glucose sensor over a period of time of about 7 days. The glucose related current (nA) collected at different time points (hours) is shown in FIG. 5A.

Figure 5B:
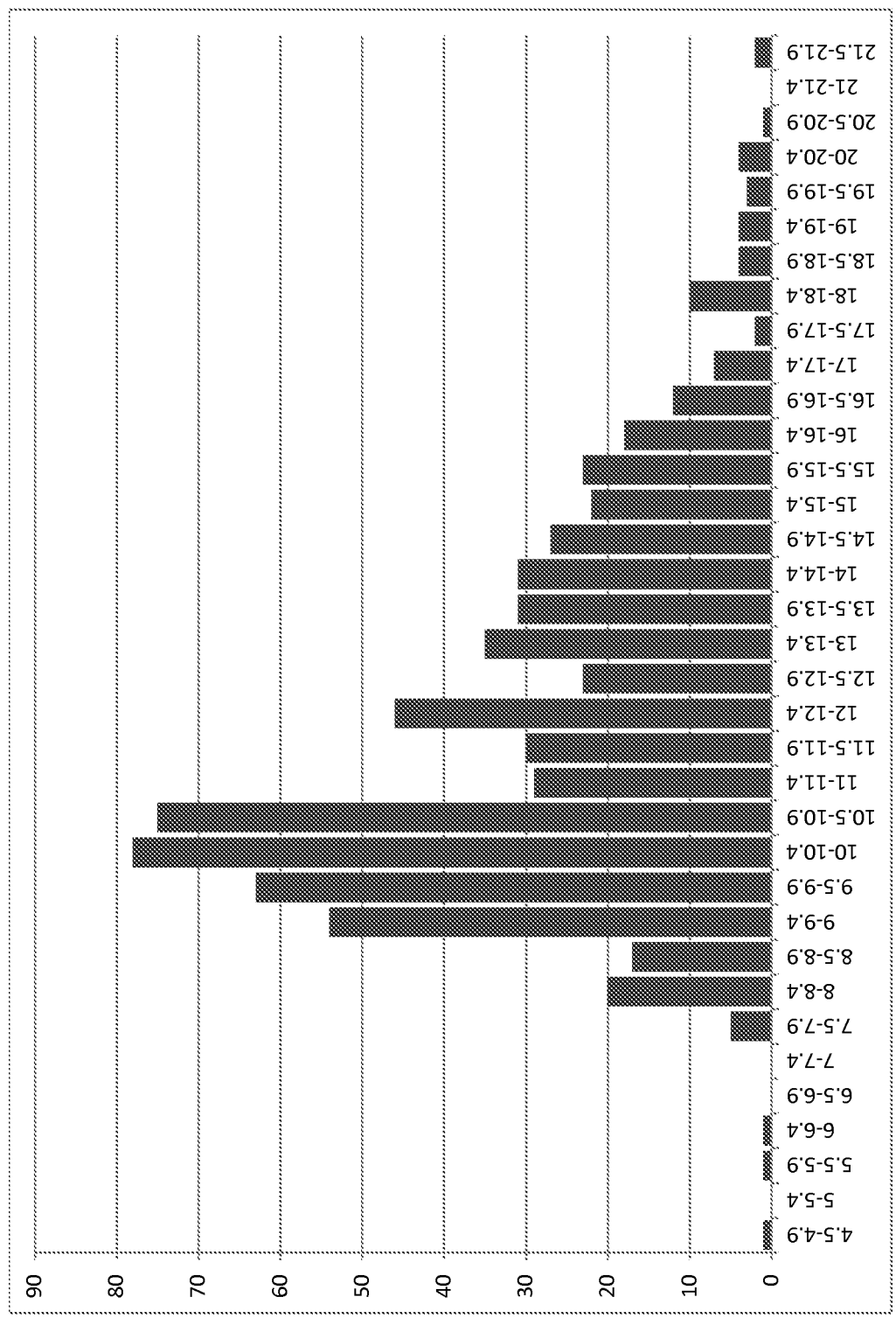
FIG. 5B is a frequency histogram of the data shown in FIG. 5A.

The glucose related current was analyzed to identify signal data points that occur most frequently within the collected data. Specifically, glucose related current values that were within a 0.5 nA range were placed in a single bin. The number of occurrences of data points within each bin was calculated and the most frequently represented bin was identified. The frequency histogram showing the number of occurrences of collected current values falling within each bin is shown in FIG. 5B. As evident from FIG. 5B, the current values ranging from 10 to less than 10.5 were identified as the most frequently occurring data points. Thus, these data points correlate to a normal physiological glucose level of about 95 mg/dL. The average signal in this bin was calculated to be 10.25 nA.

The collected glucose related signal may now be converted into a calibrated glucose level by using the formula:

Calibrated Glucose=Sensor Signal*(95/10.25)

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A computer-implemented method of improving accuracy of glucose level measurement of an in vivo positioned glucose sensor in a subject that does not have type 1 diabetes, the method comprising:
    collecting, by one or more processors, signal data from an in vivo positioned glucose sensor over a period of time, wherein the signal data is indicative of glucose levels;
    analyzing, by one or more processors, the collected signal data and identifying signal data points that occur most frequently within the collected signal data and correspond to a known physiological level for the glucose, the identified signal data points being taken from the signal data collected from the in vivo positioned glucose sensor;
    calculating, by one or more processors, a calibration factor from the identified signal data points and the known physiological level; and
    deriving, by one or more processors, glucose levels from the collected signal data using the calibration factor.

2. The method of claim 1, wherein the identified signal data points being taken from the signal data collected by the sensor were collected at a specified time of the day.

3. The method of claim 1, wherein
    the known physiological level is a normal physiological level of glucose.

4. The method of claim 1, wherein the period of time is at least two days.

5. The method of claim 1, wherein the period of time is at least one week.

6. The method of claim 1, wherein the period of time is at least two weeks.

7. The method of claim 1, wherein the collected signal data is selected from the group consisting of voltage, current, resistance, capacitance, charge, conductivity, or a combination thereof.

8. The method of claim 1, wherein analyzing the collected signal data and identifying signal data points that occur most frequently within the collected signal data and correspond to a known physiological level for the glucose comprises analyzing a subset of the collected signal data corresponding to a subset of the period of time and identifying signal data points that occur most frequently within the subset of collected data.

9. The method of claim 1, wherein the period of time is at least three weeks.

10. The method of claim 1, wherein the period of time is at least 1 month.

11. The method of claim 1, wherein the subject has pre-diabetes, impaired glucose tolerance, or non-insulin dependent type 2 diabetes.

12. A computer for improving accuracy of analyte level measurement of an in vivo positioned glucose sensor, the computer comprising:
a memory and a processor, the memory operably coupled to the processor, wherein the memory has a plurality of instructions stored thereon that, when executed, cause the processor to:
analyze signal data collected from an in vivo positioned glucose sensor over a period of time from a subject that does not have type 1 diabetes, wherein the signal data is indicative of glucose levels;
identify signal data points that occur most frequently within the collected signal data and correspond to a known physiological level for the glucose, wherein the identified signal data points are from the signal data collected from the in vivo positioned glucose sensor;
calculate a calibration factor from the identified signal data points and the known physiological level; and
derive glucose levels from the collected signal data using the calibration factor.

13. The computer of claim 12, wherein the plurality of instructions, when executed, cause the processor to identify the signal data collected by the sensor at a specified period of time of the day.

14. The computer of claim 12, wherein the known physiological level is a normal physiological level.

15. The computer of claim 12, wherein the period of time is at least two days.

16. The computer of claim 12, wherein the period of time is at least one week.

17. The computer of claim 12, wherein the period of time is at least two weeks.

18. The computer of claim 12, wherein the collected signal data is selected from the group consisting of voltage, current, resistance, capacitance, charge, conductivity, or a combination thereof.

19. The computer of claim 12, wherein the plurality of instructions, when executed, cause the processor to:
analyze a subset of the collected signal data corresponding to a subset of the period of time; and
identify signal data points that occur most frequently within the subset of collected data.

20. The computer of claim 12, wherein the period of time is at least three weeks.

21. The computer of claim 12, wherein the period of time is at least 1 month.

22. The computer of claim 12, wherein the subject has pre-diabetes, impaired glucose tolerance, or non-insulin dependent type 2 diabetes.

* * * * *